Figure 1:
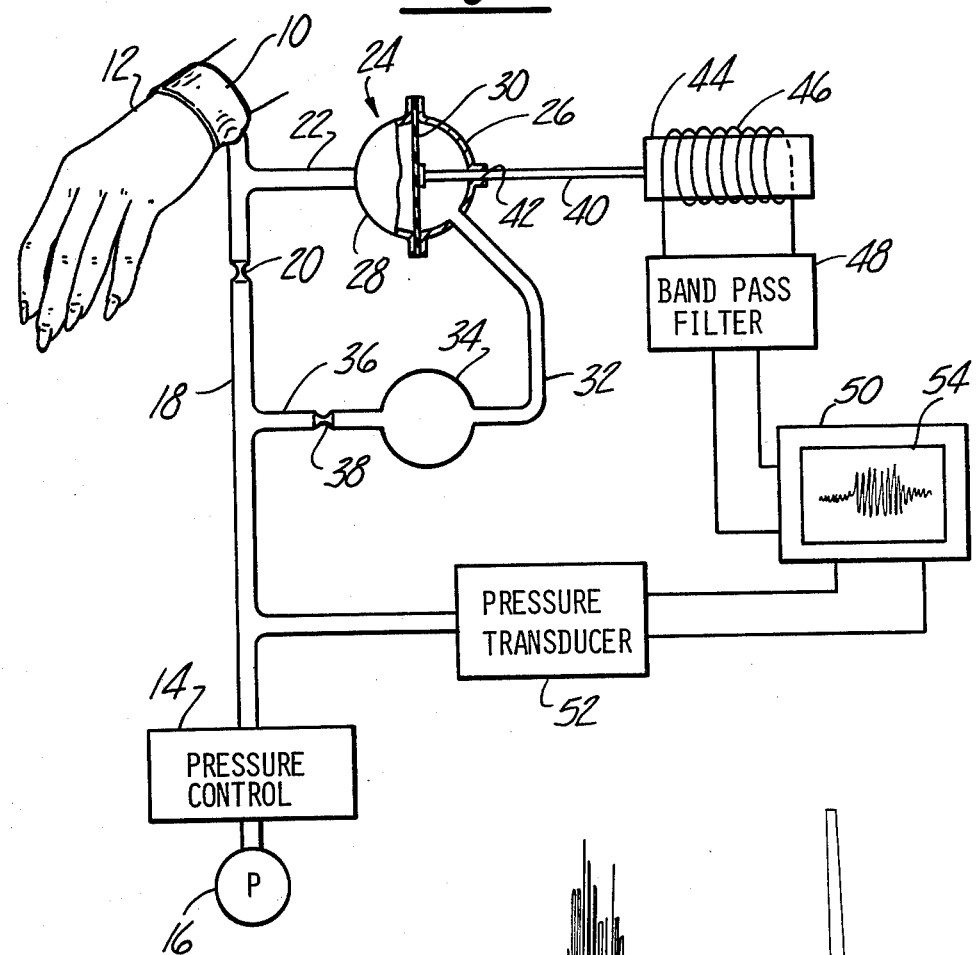

United States Patent [19]

Williams

[11] 4,206,764
[45] Jun. 10, 1980

[54] METHOD AND APPARATUS FOR ANALYZING CARDIOVASCULAR SYSTEMS

[75] Inventor: William J. Williams, Ann Arbor, Mich.

[73] Assignee: Weisman & Allen, Madison Heights, Mich.

[21] Appl. No.: 912,558

[22] Filed: Jun. 5, 1978

Related U.S. Application Data

[63] Continuation-in-part of Ser. No. 748,528, Dec. 8, 1976, Pat. No. 4,117,835.

[51] Int. Cl.$^2$ .............................................. A61B 5/02
[52] U.S. Cl. .................................................. 128/677
[58] Field of Search ................. 128/2.05 R, 2.05 A, 128/2.05 E, 2.05 M, 2.05 Q, 677–683

[56] References Cited

U.S. PATENT DOCUMENTS

| | | | |
|---|---|---|---|
| 3,482,565 | 12/1969 | Gowen | 128/2.05 A |
| 3,741,199 | 6/1973 | Sharpe | 128/2.05 M |
| 3,811,439 | 5/1974 | Brown | 128/2.05 M |
| 3,903,872 | 9/1975 | Link | 128/2.05 A |

FOREIGN PATENT DOCUMENTS 1221331 2/1971 United Kingdom ............... 128/2.05 M

*Primary Examiner*—Lee S. Cohen
*Attorney, Agent, or Firm*—Krass and Young

[57] ABSTRACT

The operation of a patient's cardiovascular system is analyzed by positioning an inflatable cuff over an extremity of the patient so that a blood vessel in the extremity experiences the cuff pressure and then modifying the pressure in the cuff through a cycle in which the vessel is occluded. A first electrical signal is generated as a function of the pressure in the cuff during the cycle and a second electrical signal is independently generated as a function of the rate of change of pressure in the cuff through use of a transducer which receives a fluid signal proportional to the pressure in the cuff and moves a core with respect to a wire coil to generate the rate of change signal. The two signals are plotted relative to one another and the resulting plot includes information relating to cardiovascular disfunctions such as arhythmia, ischemia and hypertrophy.

9 Claims, 2 Drawing Figures

METHOD AND APPARATUS FOR ANALYZING CARDIOVASCULAR SYSTEMS

REFERENCE TO RELATED APPLICATIONS

This application is a continuation-in-part of application Ser. No. 748,528, filed Dec. 8, 1976, now U.S. Pat. No. 4,117,835.

BACKGROUND OF THE INVENTION

1. Field of the Invention

This invention relates to a method for analyzing cardiovascular system dysfunction by applying a varying pressure cycle to a blood vessel and plotting the rate of change of pressure in the vessel as a function of the applied pressure and to apparatus for practicing the method employing a pressure rate of change transducer to generate an electrical signal that is plotted as the dependent vehicle.

2. Prior Art

Vascular blood pressure in the form of measurements of systolic and diastolic pressure has long been recognized as an important indicator of cardiovascular system function. Cases of hypertension or hypotension revealed by measurements of blood pressure may be caused by either or both cardiac or vascular system impairments and more definitive tests, such as the electrocardiogram may be employed to diagnose the specific cause of a detected blood pressure abnormality.

Consideration of the nature of the cardiovascular system makes it apparent that almost all changes in condition of the system will effect the nature of the blood flow through the vascular system and only a small percentage of these condition changes will appreciably modify the systolic and diastolic pressure in the vascular system. Accordingly, many or even most cardiovascular anomalies cannot be diagnosed by the conventional blood pressure measurements. This analysis has motivated us to seek some form of non-invasive vascular pressure measurement capable of detecting those anomalies in cardiovascular system operation which escape detection by present techniques.

SUMMARY OF THE INVENTION

The present invention is accordingly directed toward a method of non-invasive blood flow analysis which provides an indicator of the manner of operation of the cardiovascular system. The measurement may be used to make quantitative evaluations of cardiovascular system operation. But it more readily lends itself to use in a comparative analysis based upon changes noted between two measuremens made at separate times, in the manner of an electrocardiogram. These noted changes may either pinpoint anomalous operation of various aspects of the cardiovascular system or simply suggest some broad area of dysfunction.

The method of the present invention broadly involves generation of a plot of the rate of pressure change in a blood vessel which occurs while the vessel is subjected to a cycle of changing external pressure. In the preferred embodiment of the invention this pressure is imposed through use of an inflatable chamber, preferably in the form of a conventional blood pressure cuff, which encircles an extremity of the patient. Pressure on the cuff is thus exerted on vessels within the extremity and the pressure is cycled, preferably by automatic means, between a high value which exceeds the level at which flow through the vessel is occluded, and a low value below the diastolic pressure in the vessel.

This external pressure change occurs over a relatively long time period relative to the heartbeat, preferably from a period of ten seconds to about one minute. Since the instantaneous pressure in the cuff is in balance with the instantaneous pressure in the vessel, the vessel pressure, which changes relatively rapidly during the heart cycle relative to the slow changing cycle of the cuff pressure and the resultant rate of change of the vessel pressure, may be measured by instantaneous analysis of the pressure within the cuff. This may be done in the manner of prior art blood pressure measurement systems, such as that disclosed in Link U.S. Pat. No. 3,903,872, by employing a pressure transducer to generate an electrical signal as a function of pressure in the cuff, and then electrically differentiating this signal to derive a pressure rate of change signal. However, we have found that this arrangement produces an output signal containing a high electrical noise element since electrical noise in the output signal of the pressure transducer is interpreted as rapid pressure changes, resulting in the amplification of this noise in the output of the differentiator. The present invention accordingly contemplates use of a novel rate of change of pressure transducer employing a linear differential voltage transformer having its armature driven by a diaphragm subjected to a cuff pressure. The output signal of the differential transformer is a direct function of the rate of change of diaphragm position and accordingly is a rate change of cuff pressure.

In the preferred embodiment of the invention, which will subsequently be disclosed in detail, the dynamic range of pressures that the diaphragm is subjected to is limited by applying a balancing pressure to the side of the diaphragm opposite to that subjected to the cuff pressure. This balancing pressure may be of a constant value, so as to effectively subtract a constant from the pressure exerted on the diaphragm by the cuff, or it may be a variable pressure that corresponds to the pressure applied to the cuff by the pressurizing apparatus. In this manner the diaphragm is only subjected to pressure variations which correspond to the variations within the blood vessel and the diaphragm may be constructed of a highly resilient material so that it accurately follows these small, rapid pressure variations.

A plot of the transducer output signal as a function of applied pressure has a shape which depends upon the nature of flow through the pressurized blood vessel during the entire applied pressure cycle. Changes in the structure and operation of the cardiovascular system will produce changes in the shape of this plot. While some abnormalities in the system will result in gross deformations in the plot so that the malfunction is detectable by deviation of the plot shape from a normal characteristic form, other abnormalities may result in changes that are only detectable, by comparison with plots derived by use of the technique of the present invention, on the same patient at times prior to the inception of the abnormality. Other abnormalities will produce little or no modification of the curve and will accordingly be undetectable by the method of the present invention. In this respect the utility of the present invention is similar to that of an electrocardiogram plot.

The types of abnormalities which result in changes in the plot derived by the present invention of sufficient magnitude to be readily detectable either by comparisons with plots of normal patients or comparison with a plot derived at an earlier time from the same patient include arhythmia, ischemia and leftsided hypertrophy.

The method of the present invention is simple, painless, may be performed quickly, and does not require unusually expensive equipment. It is, therefore, ideally suited as a broad clinical screening technique, like the prior art blood pressure measurements, as well as for use as a precise diagnostic tool or a condition monitoring system.

Figure 2:
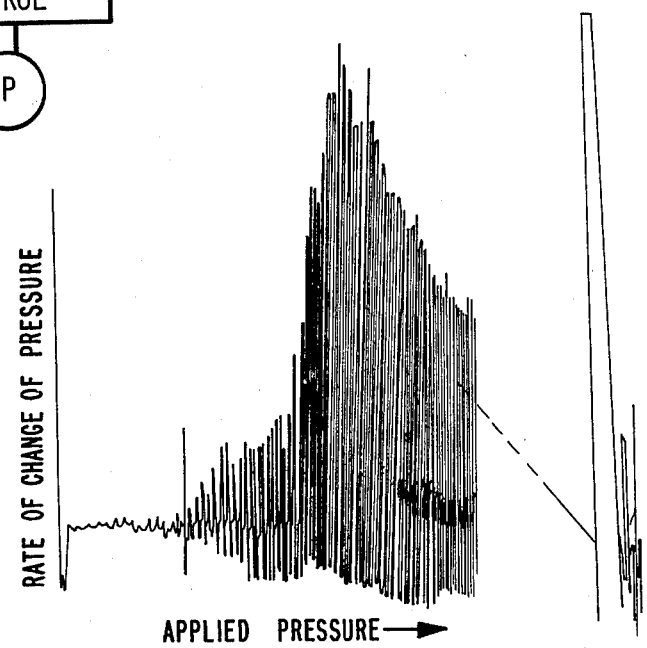

Other objectives, advantages and applications of the present invention will be made apparent by the following detailed description of a preferred embodiment of the invention. The description makes reference to the accompanying drawings in which:

FIG. 1 is a partially block, partially schematic diagram of apparatus formed in accordance with a preferred embodiment of the invention; and FIG. 2 is a plot of applied pressure versus rate of change of pressure formed in accordance with the present invention.

The preferred embodiment of the invention illustrated in FIG. 1 employs a conventional inflatable band or cuff 10 of the type used with sphygmomanometers, adapted to surround an extremity of the patient at a location where the blood vessels, preferably an artery, is close to the surface, such as the wrist 12. Other favorable locations are the upper arm or fingers. The cuff may be manually wrapped and secured or may be automatically wrapped employing apparatus such as that disclosed in copending application Ser. No. 748,528, now U.S. Pat. No. 4,117,835, entitled "Method and Apparatus for Blood Pressure Measurement".

The pressure in the cuff 10 is modified by a pressure control system 14 powered by an air pump 16. The pressure control system 14 is connected to the cuff by an air line 18 containing a restricting orifice 20. The pressure control system 14 is adapted to undergo a cycle wherein it first raises the pressure in the cuff 10 to a level which restricts the blood vessels in the patient's wrist 12 sufficiently to occlude the vessels and prevent the passage of blood therethrough. The pressure is then gradually lowered, allowing blood flow to resume through the vessels, until no appreciable pressure is exerted on the patient's extremity. The cycle time from the point of attainment of maximum pressure until minimum pressure is attained may range from 10 seconds to as long as a minute but shorter cycles times in the range of 10 to 30 seconds are preferred.

During the pressure cycle the pressure within the cuff 10 will tend to be at equilibrium with the pressure within the blood vessels in the wrist. Effectively, the blood pulsing through the elastic vessels will cause the wrist volume to expand and exert pressure on the cuff, instantaneously raising the pressure on the cuff. The instantaneous pressure within the cuff will accordingly be the sum of the pressure applied from the pressure control system 14 plus the instantaneous variations resulting from the expansion of the blood vessels. The restricting orifice 20 will tend to minimize the effect of these instantaneous pressure variations on the flow line 18 beyond the orifice.

The instantaneous pressure within the cuff 10 is communicated through a cuff pressure flow line 22, located downstream of the orifice 20, to one side of a rate of change of pressure transducer, generally indicated at 24. The transducer 24 consists of a pair of flanged hemispherical sections 26 and 28 connected together at their flanges and sandwiching a flexible diaphragm 30 between them. The diaphragm 30 divides the transducer 24 into a pair of hemispherical sections. The diaphragm 30 is preferably formed of a highly resilient elastomer.

The cuff pressure flow line 22 is connected to the hemisphere 28 to exert pressure on one side of the diaphragm 30. The pressure on the other side of the diaphragm 30 is derived from a flow line 32 which connects to an accumulator volume 34. The accumulator 34 is connected to the pressure control 14 via a portion of flow line 18 and a flow line 36 which contains a second flow restricting orifice 38. Accordingly, the pressure in the accumulator 34 broadly follows the pressure exerted by the control 14 and is isolated from the cuff pressure by the restricting orifice 20. The accumulator volume 34 tends to minimize pressure changes in the transducer hemisphere 26 caused by variations in the position of the diaphragm 30.

The diaphragm 30 therefore has a pressure exerted on one of its sides which is equal to the pressure in line 18 generated by the pressure control system 14, and a pressure on its opposite side which is equal to the pressure within the cuff 10. Since the pressure in the cuff 10 is a summation of the pressure from the control system 14 plus pressure variations resulting from blood flow through the vessels in the wrist 12, the differential pressure imposed on the diaphragm 30 is substantially equal to the pressure component caused by blood flow through the vessels of the wrist. Diaphragm 30 is designed to be sensitive to this differential pressure and to undergo its maximum deflection when the pressure contribution of the blood flow through the wrist vessels is at a maximum.

A rod 40 passes through a sliding seal 42 formed in the transducer hemisphere 26 and has one end connected to the diaphragm 30 and its exterior end connected to a permanent magnet 44. A spiral coil of conductive wire 46 surrounds the magnet 44 so that motions of the magnet cause the flux of the magnet to be passed transversely of the conductors of the coil and thereby induce electric currents in the coil. These currents have an instantaneous amplitude proportional to the instantaneous rate of the motion of the magnet 44. The currents are thus proportional to the continuous rate of change of position of the diaphragm 30 and accordingly to the continuous rate of change of the blood pressure within the vessels surrounded by the cuff 10. The coil 46, along with the sensor 44, act as a rate of change of pressure transducer.

The output of the coil 44 is provided to a band pass filter 48 which preferably has a band width from approximately 0.6 hz to 20 hz. This acts to filter out very gross changes resulting from patient movement or the like and any contribution to the transducer signal rising from the pressure generated by the pressure control 14. It also filters out signals beyond about the 20th harmonic of the pulse rate which may be regarded as noise signals.

The output of filter 48 is provided to the Y axis controls of an X-Y recorder 50. Alternatively, an oscilloscope or other form of display device might be employed.

The X axis terminals of the plotting device 50 are driven by a signal generated by a conventional pressure transducer 52 connected to the flow line 18 so as to experience the pressure generated by the control system 14.

The display device 50 thus generates a plot 54 which is a function of the rate of change of pressure within the cuff 10, or the vessels in the wrist 12 as a function of the pressure applied to the cuff by the control system 14. The use of the direct rate of change of pressure transducer 24 and its associated sensor 44, 46, eliminates noise components which would be generated if more conventional techniques were used so as to provide a clear plot that mirrors the operation of the cardiovascular system.

The plot 54 is shown in enlarged scale in FIG. 2. The cuff pressure is displayed along the X-axis with maximum pressure, somewhat above systolic pressure, at the origin. Accordingly, the cuff pressure decreases to the right. The plot may be considered to have three broad areas: a first wherein the cuff pressure is above the systolic pressure, a second wherein the cuff pressure is between systolic and diastolic pressures, and a third wherein the cuff pressure is below the diastolic pressure. The transition between the first and second regions is characterized by a sudden increase in the rate of change of pressure values. Similarly, the transition between the second and third regions is characterized by a substantial decrease in the rate of change of pressure. As disclosed in my copending application Ser. No. 748,528, now U.S. Pat. No. 4,117,835, the systolic and diastolic pressures may be analyzed by detection of these points of rapid increase and decrease in the rate of change with decreasing cuff pressure.

More centrally to the present invention, the total shape of the curve 54 is dependent on the entire nature of the cardiovascular system. For example, heartbeat frequency variations known as cardiac arrythmia will produce curves having an irregular spacing between the vertical traces associated with individual beats. An examination for this defect may involve a prolonged pressure cycle with the period between the systolic and diastolic pressures lengthened to allow detection of arrythmias occurring over the greater time period. The X-axis scale of the recording might also be increased relative to that illustrated in FIG. 2 in order to reveal the prominence of heartbeat rate irregularities.

Dysfunctions of blood supply to the heart as may be caused by coronary arterial heart disease or the like, i.e., ischemia, will result in a distortion of the displacement of the curve about a horizontal axis through the line of no rate of change of pressure. Thus the generation of negative values of pressure change is important to the practice of the present invention insofar as the detection of these anomalies is concerned.

Myocardial hypertrophy (left-sided hypertrophy in particular) will result in a decrease in the range of the curve along the Y-axis. Other disfunctions such as variations in compliance of the artery, valvular dysfunctions and the like, will produce other variations in the curve.

As has been noted, some of these dysfunctions will produce such appreciable variation with respect to a normal curve that a single plot of the patient suffering from such a dysfunction will reveal a departure from the plot of a normal person to signal a dysfunction. Other dysfunctions will produce more subtle variations in the plot which may only be detectable by comparison with a previous plot derived from the same patient before onset of the dysfunction.

The embodiments of the invention in which an exclusive property or privilege is claimed are defined as follows:

1. The method of analyzing the functioning of the cardiovascular system in a mammal comprising:

applying an inflatable pressure chamber against the body of the mammal in proximity to a blood vessel so that the pressure within the chamber is exerted against the vessel;

gradually varying the pressure in the chamber between a value at which the vessel is occluded to prevent blood flow therethrough and a pressure value below the diastolic pressure in the vessel over a time period extending over a number of heartbeats;

continuously generating a plot of the instantaneous rate of change of pressure in the chamber as a function of pressure during such pressure change time period;

and detecting anomalies in the plot which are related to anomalies in the functioning of the mammal's cardiovascular system.

2. The method of claim 1 in which the time period over which said pressure is varied comprises an interval between ten seconds and one minute.

3. Apparatus for generating a plot of information related to the functioning of the cardiovascular system of a mammal comprising:

an inflatable pressure chamber adapted to be positioned on the body of the mammal in proximity to a blood vessel so that a pressure is exerted on the exterior of the vessel which is a direct function of the pressure within the chamber;

means for modifying the pressure within the chamber through a cycle of varying pressure between a level which causes occlusion of the vessel and a level of pressure below diastolic pressure in the vessel over a time period of at least several heartbeats;

means for generating a first electrical signal proportional to the average pressure within the chamber;

means for continuously generating a second electrical signal proportional to the instantaneous rate of change of pressure within the chamber;

and means for generating a plot of the first electrical signal as a function of the second electrical signal during the cycle.

4. The apparatus of claim 3 in which the means generating said second electrical signal comprises a transducer in communication with the pressure within the chamber.

5. The apparatus of claim 4 wherein said transducer includes a diaphragm and means subjecting said diaphragm to the pressure within the chamber so as to move as a function of the pressure within the chamber, said transducer also includes means for generating a magnetic field and a coil disposed in the field, and means for creating relative movement between the coil and the field as a function of changes in position in said diaphragm.

6. The apparatus of claim 5 wherein said means subjecting said diaphragm to chamber pressure subjects one side of the diaphragm to the pressure within the chamber and further including means subjecting the other side of the diaphragm to the average pressure applied to the chamber.

7. The apparatus for analyzing the functioning of the cardiovascular system in a mammal comprising:

an inflatable cuff adapted to encircle an extremity of the mammal;

means for inflating the cuff including means for varying the pressure in said cuff over a time period;

a transducer having a chamber divided into two sections by a resilient diaphragm;

a fluid conduit connecting one of the diaphragm sections to the interior of the cuff;

fluid conduit means connecting the other of the diaphragm sections to a source of pressure equal to the average pressure applied to the cuff;

and means for continuously generating a signal representative of the instantaneous rate of motion of the diaphragm and means recording said signal over said time period.

8. The apparatus of claim 7 wherein said means for generating a signal which is a function of the rate of motion of the diaphragm generates an electrical signal.

9. The apparatus of claim 8 wherein said means for generating an electrical signal as a function of the rate of motion of the diaphragm includes a magnet and a wire coil and means for moving the magnet relative to the coil as the diaphragm moves so as to continuously generate electrical signals in the coil as a function of the instantaneous rate of motion of the diaphragm.

* * * * *